United States Patent
Krieg et al.

(10) Patent No.: US 7,327,138 B2
(45) Date of Patent: Feb. 5, 2008

(54) METHOD FOR GENERATING AN MR ATLAS AND FOR MR IMAGING USING SAME

(75) Inventors: Robert Krieg, Nürnberg (DE); Ralf Ladebeck, Erlangen (DE); Oliver Schreck, Bamberg (DE)

(73) Assignee: Siemens Aktiengesellschaft, Munich (DE)

( * ) Notice: Subject to any disclaimer, the term of this patent is extended or adjusted under 35 U.S.C. 154(b) by 88 days.

(21) Appl. No.: 11/222,876

(22) Filed: Sep. 9, 2005

(65) Prior Publication Data

US 2006/0058641 A1    Mar. 16, 2006

(30) Foreign Application Priority Data

Sep. 10, 2004    (DE)    ................ 10 2004 043 889

(51) Int. Cl.
*G01V 3/00*    (2006.01)
(52) U.S. Cl. ...................... 324/307; 324/322
(58) Field of Classification Search ........ 324/300–322; 600/407, 410, 422, 4
See application file for complete search history.

(56) References Cited

U.S. PATENT DOCUMENTS 6,740,883 B1    5/2004    Stodilka et al.
6,836,113 B2 *  12/2004   Zhang ......................... 324/307
7,102,352 B2 *  9/2006    Hinks et al. ................. 324/318
2003/0139659 A1    7/2003    Dale et al.

OTHER PUBLICATIONS

"A Method for Coregistration of PET and MR Brain Images," Anderson et al. The Journal of Nuclear Medicine, vol. 36, No. 7, Jul. 1995, pp. 1307-1315.
"Magnetic Resonance Imaging-guided Attenuation and Scatter Corrections in Three-Dimensional Brain Positron Emission Tomography," Zaidi et al., Med. Phys., vol. 30, No. 5, May 2003, pp. 937-948.

* cited by examiner

*Primary Examiner*—Brij B. Shrivastav
(74) *Attorney, Agent, or Firm*—Schiff Hardin LLP

(57) ABSTRACT

A nuclear-medical image is generated from a nuclear-medical data set that can be acquired with a dual modality tomography apparatus, which has both a scanner for acquisition of magnetic resonance images and a scanner for acquisition of nuclear-medical data sets within a common acquisition volume. A nuclear-medical data set and an MR image are thereby acquired, and a nuclear-medical magnetic resonance atlas is provided with a reference MR data set of the region of a reference patient to be imaged and a corresponding correction data set. A transformation that maps the reference MR data set to the MR image is generated and applied to the correction data set to generate a transformed correction data set that is registered with the nuclear-medical data set. The corrected nuclear-medical image is subsequently calculated from the transformed correction data set and the nuclear-medical data set.

13 Claims, 2 Drawing Sheets

| | | | 5 |
|---|---|---|---|
| $\Delta I_A: 1 < I \le 0.8$ | | $S_A$ | $A_A$ |
| $\Delta I_B: 0.8 < I \le 0.7$ | | $S_B$ | $A_B$ |
| ⋮ | | ⋮ | ⋮ |
| $\Delta I_E: 0.1 < I \le 0$ | | $S_E$ | $A_E$ |

$$I_{ijk} = \begin{cases} I_A\,;\, S_A,\, A_A\,:\, P(I_A) = P_A \\ \quad\vdots \\ I_E\,;\, S_E,\, A_E\,:\, P(I_E) = P_E \end{cases}$$

METHOD FOR GENERATING AN MR ATLAS AND FOR MR IMAGING USING SAME

BACKGROUND OF THE INVENTION

1. Field of the Invention

The present invention concerns a nuclear-medical magnetic resonance atlas as well as a method for generation of such a magnetic resonance atlas. The invention also concerns a method for generation of a nuclear-medical image with such a magnetic resonance atlas.

2. Description of the Prior Art

In addition to computed tomography (CT) and magnetic resonance tomography (MRT), nuclear medicine (NM) is an important modality for imaging diagnostics. NM supplies primary and/or additional diagnostic results and thus forms an important component piece in the overall diagnostic scene. NM uses radioactive isotopes for qualitative or quantitative analysis of, among other things, diffusion and metabolic processes. A specific enrichment of the various isotopes in the organs enables a sensitive functional diagnostic of nearly all organ systems. Positron emission tomography (PET) or single photon emission computer tomography (SPECT) are examples of modern nuclear-medical modalities for medical imaging.

In NM imaging, among other things information regarding scattering and attenuation of the detected radiation or particles must be accounted for in the evaluation of NM data. The required information can be acquired, for example, with a test measurement. An alternative is to draw the information from a registration of the NM data with an NM atlas; this means that the NM data are superimposed with an NM atlas image containing, for example, the attenuation coefficients.

The use of an anatomical NM atlas (more precisely a PET atlas) for scatter and attenuation correction of PET images is known, for example, from U.S. Pat. No. 6,740,883. For this purpose, a three-dimensional computer model with a PET image is superimposed and aligned as a PET atlas. The computer model represents the density distribution within the acquisition region of interest and is generated by averaging of existing transmission or CT images of a number of patients. In one embodiment, the computer model includes a functional component that simulates a PET or SPECT image of the acquisition region and an anatomical component that simulates a transmission exposure of the acquisition region. For a uniform scatter and attenuation correction, the anatomical component of the computer model is segmented into tissue types, with which attenuation coefficients are in turn associated.

Furthermore, a pathology-related NM atlas can be used that, for example, is indexed to the clinical appearance [pathological pattern] of a stroke. Pathology-dependent changes of the anatomy are thereby accounted for in the NM atlas. Such a computer model also can be generated by segmentation of an MR atlas image, meaning that, for example, a SPECT atlas image and an anatomical atlas image are generated from the MR atlas image. For example, the former can correspond to a SPECT measurement and the latter to a transmission measurement.

An example for an MR atlas is disclosed in United States Patent Application Publication Ser. No. 2003/0139659. The MR atlas contains representative values of MR properties of an MR examination of a "reference patient," and optionally contains tissue-specific probabilities. The MR atlas can be used, for example, together with a test measurement in order to establish a specific geometry of slices of an MR measurement to be measured. For example, using the MR atlas a section guide (slice guide) generated using an MR atlas image for each patient can be transferred onto an MR exposure of a patient. For this purpose, a rotation and translation transformation that maps the test MR image to the MR atlas image is determined from a comparison of a test MR image with the MR atlas image. The position of the patient is thereby known relative to the reference patient and, by means of the rotation, dilation, compression and translation transformation, predefined standard sections can be automatically transferred from the geometry of the atlas/reference patient to the patient in the MR apparatus and MR data then can be suitably acquired.

As noted, NM data can be processed into an NM image with an NM atlas for scatter and attenuation correction. One difficulty in the use of such an NM atlas is the low image quality of, for example, functional PET images in which, for example, only the function of a small region in the brain is shown. A registration of, for example, a PET image with a PET atlas image thus has inaccuracies associated therewith.

The acquisition of, for example, CT or MR images, as well as nuclear-medical images, is possible with a system known as a dual modality tomography apparatus. In combination with a CT apparatus, the required information about scatter and attenuation coefficients of the examined tissue can be directly acquired from the x-ray exposures. This means that the test measurement is omitted due to the ability to register the NM and CT measurements and to obtain the required information directly from the CT data. This is not directly possible in a combination of NM apparatus and MR apparatus. In particular, tissue differentiation between bones, lungs and soft anatomy (of which bones are not directly imaged in the MR image) is necessary for the determination of the attenuation coefficients.

The required information about the curvature of bones, however, can be acquired by manual or automatic segmentation. For example, for this purpose a patient is examined with a number of specially-parameterized MR measurement sequences that, for example, makes use of different parameters such as T1 or T2. MR images thus are acquired in which various tissue types are shown differently. The tissue types then can be classified with a segmentation algorithm and provided with attenuation coefficients. An attenuation correction matrix is subsequently created for the examined region. Zaldi et al. describe such a procedure in "Magnetic resonance imaging-guided attenuation and scatter corrections in three dimensional brain position emission tomography", Medical Physics, Vol. 30 (#5), May 2003, p. 937-947.

A method for superimposition of PET and MR brain images is known from Jesper et al.: "A Method of Coregistration of PET and MR brain images", (1995) The Journal of Nuclear Medicine, Vol. 36, No. 7, p. 1307-1315. A simulated PET image is thereby generated from an MR image via segmentation and by association of "acquisition" values. A transformation that maps the two images one over the other is determined using the comparison of the simulated PET image with the measured PET image. This transformation is subsequently applied to the superimposition of MR image and PET image.

SUMMARY OF THE INVENTION

An object of the invention is to simplify and to improve the scatter and attenuation correction of NM raw data, compared to conventional techniques.

This object is achieved in accordance with the invention by a nuclear-medical magnetic resonance atlas for correction of nuclear-medical data in the image generation of a nuclear-medical image, the atlas containing reference MR data set and a correction data set, with correction data of the correction data set being associated with the reference MR data set.

An advantage of such an NM-MR atlas is in the association of high-resolution MR data with information required for image generation that is present, for example, in the form of attenuation and/or scatter coefficients due to the correction data set. For example, the reference MR data set can contain a data point for every spatial coordinate (image point) of a reference MR atlas image. The data point can be, for example, at least one intensity value that is associated with a measurement sequence. The association preferably ensues for each data point of the reference MR data set, meaning that an attenuation coefficient is associated with each data point. For this purpose, the reference MR data set and the correction data set are stored in a common matrix. Alternatively, the association can ensue indirectly using intensity values stored in the data points. Because the intensity values represent as grey values in the MR image of a tissue type, the corresponding attenuation and/or scatter coefficient of the associated (most probable) tissue type can also be associated with an intensity interval. For example, the correction data set then corresponds to an association of intensity intervals with correction coefficients. The inventive atlas also enables implementation of the registration of the correction data set on an NM image with the aid of the reference MR data set.

The above object also is achieved in accordance with the invention by a method for generation of a nuclear-medical magnetic resonance atlas wherein a reference MR data set is provided in the form of an average MR image of a region to be imaged. This can, for example, occur by averaging a number of MR images of various patients for generation of the reference MR data set. A correction data set is subsequently associated with the reference MR data set. The correction data set is acquired from a nuclear-medical test measurement of at least one patient or from a reference CT data set or from at least one CT image.

The method has the advantage that the nuclear-medical magnetic resonance atlas can be at least partially generated from known components. For example, the aforementioned MR atlas can be used as a reference MR data set. Due to the low requirements for the precision of the correction, the correction data set can inventively result from a nuclear-medical test measurement of at least one patient or of a number of averaged patients or can be determined from known CT data sets.

The above object also is achieved by a method for generation of a nuclear-medical image from a nuclear-medical data set wherein the nuclear-medical data set is acquired with a dual modality tomography apparatus that includes both a scanner for acquisition of magnetic resonance images and a scanner for acquisition of nuclear-medical images within a common acquisition volume. In the method, the nuclear-medical data set of a region of a patient to be imaged is acquired. An MR data set of the same region to be imaged is acquired beforehand, simultaneously or subsequently. A registration of the MR data set and a reference MR data set of the nuclear-medical magnetic resonance atlas now ensue with the aid of the nuclear-medical magnetic resonance atlas. The registration is accomplished by a transformation of at least one of the images. This transformation is now applied to the correction data set so that this set and the nuclear-medical data set are superimposed. A corrected nuclear-medical image is subsequently calculated from the transformed correction data set and the nuclear-medical data set. A known geometric relation of the NM exposure and of the MR exposure is assumed. This is inherent to the system given the use of the dual modality tomography apparatus since the geometric relation of an MR acquisition region to an NM acquisition region is established by the design. Various methods for alignment of the exposures are known given measurements implemented on separate systems. For example, the region to be examined can be clamped in a fixed manner in a device. The device can then be brought into a known position in the acquisition volumes, for example with the aid of a laser positioning system. Alternatively, the alignment can be effected with the aid of image markers in the image processing. The image markers should be well-mapped in both exposures and be fixed with regard to their position relative to the examined region.

An advantage of this method is that a magnetic resonance examination and a nuclear-medical examination can be mutually implemented in a simple manner. A further advantage of the method is that, with the aid of the nuclear-medical magnetic resonance atlas, the information of the magnetic resonance image can be used to simplify and to improve the generation of the nuclear-medical image.

In embodiments of the method and of the NM-MR atlas, data of the reference MR data set include intensity values that correlate with tissue types. The correction data set preferably includes tissue-specific attenuation and/or scatter coefficients that are in particular associated with the intensity values.

DESCRIPTION OF THE PREFERRED EMBODIMENTS

Figure 1:
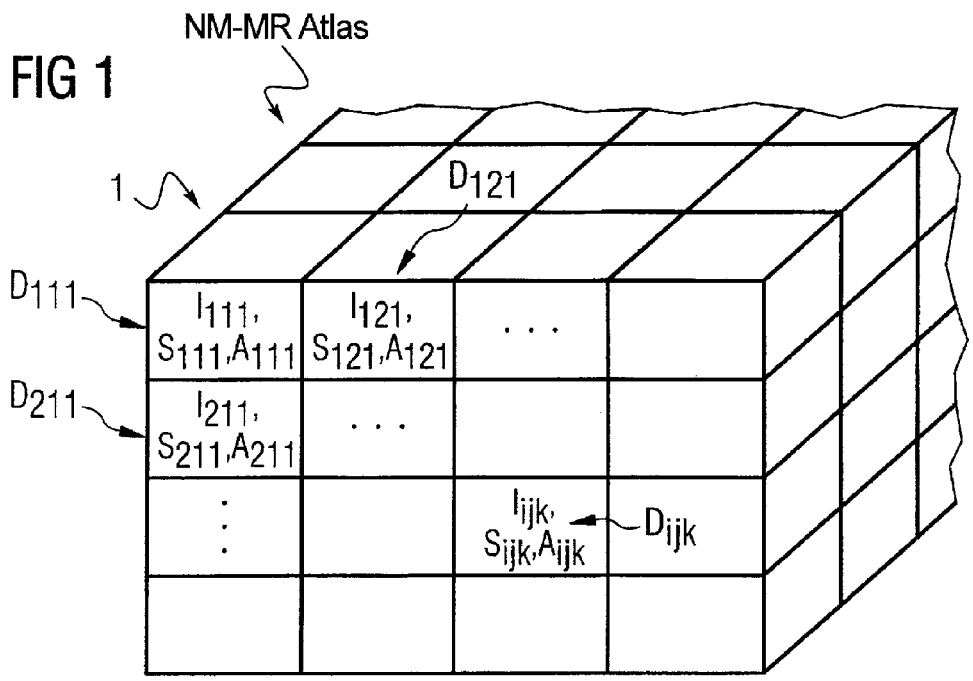
FIG. 1 schematically illustrates a nuclear-medical magnetic resonance atlas in matrix form in accordance with the invention.

FIG. 1 schematically shows an exemplary NM-MR atlas in matrix form according to the invention. At least one intensity value $I_{ijk}$ is associated with each data point $D_{ijk}$ of the NM-MR atlas 1, corresponding to an image point in the MR image of the reference MR data set. This intensity value $I_{ijk}$ is tissue-specific and would be allocated with a grey value in a representation of the MR image, for example on a monitor. The. NM-MR atlas 1 additionally contains correction coefficients $S_{ijk}, A_{ijk}$ that are necessary for correction of nuclear-medical data. In FIG. 1 they form a correction data set that is linked with the intensity values $I_{ijk}$ of each data point. For example, an attenuation coefficient $A_{ijk}$ and a scatter coefficient $S_{ijk}$ are associated with each data point.

Figure 2:
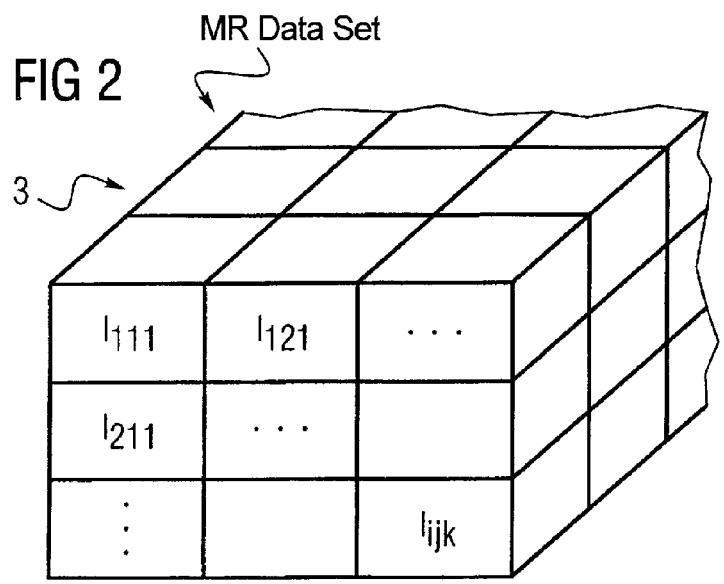
FIG. 2 illustrates a reference MR data set oriented on image points.
Figures 3, 4, 5:
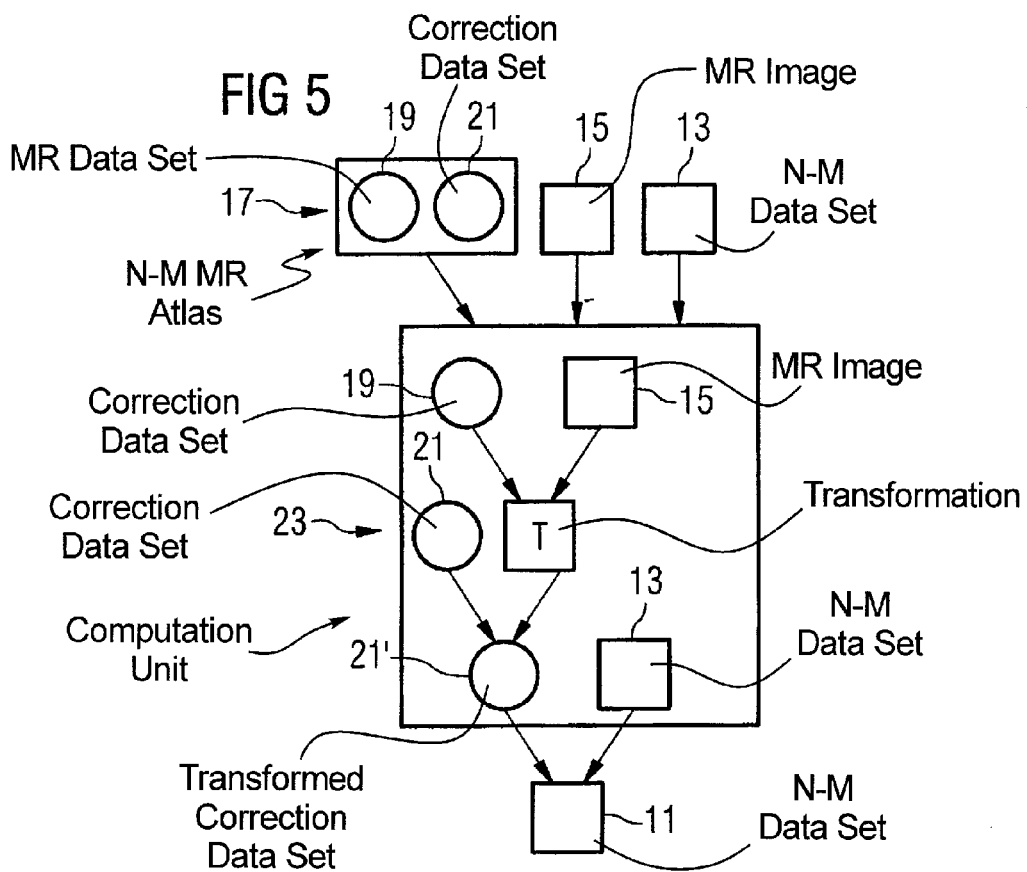
FIG. 3 illustrates an association of intensity intervals of the reference MR data set (for example from FIG. 2) with attenuation and scatter coefficients in accordance with the invention.
FIG. 4 illustrates a probability-based association of attenuation and scatter coefficients with intensity intervals of a reference MR data set in accordance with the invention.
FIG. 5 is a flowchart for generation of a nuclear-medical image with the aid of a nuclear-medical magnetic resonance atlas in accordance with the invention.

In addition to the fusion of correction data set and reference MR data set oriented on image points according to FIG. 1, both data sets can be mapped separately. This is shown in FIGS. 2 and 3. The component reference MR data set 3 is shown in the form of an MR atlas as a matrix in FIG. 2. Each data point represents the intensity value $I_{ijk}$ of the tissue present in the respective image point. The generation of such an MR atlas is, for example, described in the aforementioned United States Patent No. 2003/0139659.

According to the functionality table 5 shown in FIG. 3, various scatter coefficients $S_A, \ldots S_E$ and attenuation coefficients (absorption coefficients) $A_A, \ldots A_E$ are associated with various intensity intervals $\Delta I_A, \ldots \Delta I_E$.

The association of scatter and absorption coefficients can additionally be probability-based. According to FIG. 4, a representative intensity value $I_A$ can, for example, be associated with the data point $D_{ijk}$, whereby the intensity value $I_A$ lies in the intensity interval $\Delta I_A$ and exists in the data point $D_{ijk}$ with a probability $P_A$. Scatter and/or attenuation coefficients $S_A, A_A$ are correspondingly associated with the data point $D_{ijk}$ with the probability $P_A$. The probability-based association can ensue for a plurality of intensity intervals $\Delta I_A, \ldots \Delta I_E$.

Various procedures are conceivable according to which a reference patient can be created for the atlas. For the MR atlas disclosed in in United States Patent Application Publication Ser. No. 2003/01399659, approximately 100 patients were examined whose MR images were averaged into a reference MR image of a reference patient. In an extensive approach, this method can be repeated for the NM-MR atlas in that MR images (for the data set MR atlas) on the one hand and CT images or NM attenuation images on the other hand of an identical patient group are acquired. The correction coefficients are then calculated from the CT images. An average CT reference patient is additionally generated so that the correction coefficients can also be registered with the MR atlas with the aid of the transformation of CT reference patient to MR reference patient.

Due to the low requirements for the precision of the attenuation correction, the following simplifications can alternatively be effected:

1. The same patients need not be examined both with CT and MR apparatuses. Instead, different patient groups are examined and the reference patients are individually determined for both data sets. This has the advantage that existing MR reference atlases can be reused.
2. In addition to the first simplification, a distinctly smaller number of patients are used for the CT examinations. As an alternative to CT examinations, direct NM test measurements (for example PET attenuation measurements) or, respectively, their data can naturally also be used. A fusion of PET data with MR data is distinctly more complicated, but it only has to be conducted once.

FIG. 5 shows a flowchart for explanation of the method for generation of a nuclear-medical image 11 from a nuclear-medical data set 13. For example, this was measured with a dual modality tomography apparatus that has a scanner for acquisition of a magnetic resonance image and a scanner for acquisition of a nuclear-medical image within a common acquisition volume. The geometric relation of image points of the NM and MR measurements is thus known.

In a first step, the nuclear-medical data set 13 and an MR image are measured in an identical acquisition volume in an NM measurement and in an MR measurement. Among other things, a correction of scattering and attenuation of the measured radiation or particles is now necessary for evaluation of the nuclear-medical data set 13. For this purpose, an inventive nuclear-medical magnetic resonance atlas 17 is read. The atlas contains a reference MR data set 19 and a correction data set 21. A calculation of the Nm image 11 now ensues with the nuclear-medical magnetic resonance atlas 17 in a computation unit 23 of the dual modality tomography apparatus.

A transformation T of the reference MR data set 19 on the measured MR image 15 is thereby calculated. Due to the measurement in the same acquisition volume with the same apparatus, the MR image 15 is registered with the NM data set 13, meaning that their geometric association is known. Taking this into account, the calculated transformation T can now be applied to the correction data set 21 so that a transformed correction data set 21' and the nuclear-medical data set 13 are registered. The required information about attenuation and/or scattering is thus known at each data point of the nuclear-medical data set 13. The corrected nuclear-medical image 11 is subsequently calculated from the transformed correction data set 21' and the nuclear-medical data set 13.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating a nuclear-medical image from a nuclear-medical data set, comprising the steps of:
    acquiring a nuclear-medical data set of a region of a patient with a nuclear-medical data acquisition apparatus, and acquiring a magnetic resonance image of said region with a magnetic resonance imaging apparatus;
    providing an electronically-stored nuclear-medical magnetic resonance atlas comprising a reference magnetic resonance data set of said region and a correction data set for said region;
    electronically generating a transformation that maps said reference magnetic resonance data set on said magnetic resonance image;
    electronically applying said transformation to said correction data set to generate a transformed correction data set, and registering said transformed correction data set with said nuclear-medical data set; and
    electronically calculating a corrected nuclear-medical image from the transformed correction data set and the nuclear-medical data set.

2. A method as claimed in claim 1 comprising acquiring said nuclear-medical data set and said magnetic resonance image in a known geometric relation to each other.

3. A method as claimed in claim 2 comprising producing said known geometric relation by markers that are identifiable in each of said nuclear-medical data set and said magnetic resonance image.

4. A method as claimed in claim 2 comprising producing said known geometric relation by respectively positioning the patient in the nuclear-medical data acquisition apparatus and the magnetic resonance imaging apparatus.

5. A method as claimed in claim 2 comprising producing said known geometric relation by acquiring said nuclear-medical data set and said magnetic resonance image using a dual modality tomography apparatus comprising said nuclear-medical data acquisition apparatus and said magnetic resonance imaging apparatus, in which the patient is identically positioned during acquisition of each of said nuclear-medical data set and said magnetic resonance image.

6. A method for generating a nuclear-medical magnetic resonance atlas, comprising the steps of:

generating and storing a reference magnetic resonance data set representing a magnetic resonance image of a region, by averaging a plurality of magnetic resonance images of said region of a plurality of different patients;

generating a correction data set acquired from a nuclear-medical test measurement of a patient from a correction data set source selected from the group consisting of a reference computed tomography data set of said region and at least one computed tomography image of the region; and electronically storing and linking said correction data set with said reference magnetic resonance data set, to form an atlas for said region, and making said atlas electronically available as an atlas output.

7. A method as claimed in claim 6 comprising generating said magnetic resonance data set as a plurality of intensity values, and generating said correction data set as a plurality of coefficients selected from the group consisting of attenuation coefficients and scatter coefficients.

8. A method as claimed in claim 7 comprising electronically merging said magnetic resonance data set and said correction data set into a single electronic data set comprising a matrix of data points, with at least one of said intensity values at least one of said coefficients being associated with each data point, and electronically storing said single data set.

9. A computer-readable medium encoded with a data structure comprising a magnetic resonance atlas for correction of nuclear-medical data to generate a nuclear-medical image, said atlas comprising a reference magnetic resonance data set and a correction data set associated with said reference magnetic resonance data set.

10. A computer-readable medium as claimed in claim 9 wherein said reference magnetic resonance data set comprises data points each representing at least one intensity value correlated with a tissue type.

11. A computer-readable medium as claimed in claim 10 wherein each data point represents a plurality of intensity values respectively obtained with a plurality of magnetic resonance data acquisition sequences.

12. A computer-readable medium as claimed in claim 10 wherein said correction data set comprises tissue-specific coefficients, selected from the group consisting of attenuation coefficients and scatter coefficients, respectively associated with each intensity value.

13. A computer-readable medium as claimed in claim 9 wherein said reference magnetic resonance data set and said correction data set are merged into a single data set.

* * * * *